(12) United States Patent
Mutel et al.

(10) Patent No.: US 6,548,522 B1
(45) Date of Patent: Apr. 15, 2003

(54) METHOD FOR TREATING CONDITIONS RELATED TO THE GLUTAMATE RECEPTOR USING CARBOXYLIC ACID AMIDE DERIVATIVES

(75) Inventors: Vincent Mutel, Mulhouse (FR); Eric Vieira, Allschwil (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 10 days.

(21) Appl. No.: 09/669,583

(22) Filed: Sep. 26, 2000

(30) Foreign Application Priority Data

Oct. 12, 1999 (EP) .............................................. 99120327

(51) Int. Cl.[7] ........................ A61K 31/44; A61K 31/135
(52) U.S. Cl. ........................ 514/357; 514/351; 514/649
(58) Field of Search ................ 514/648, 351, 514/357

(56) References Cited

U.S. PATENT DOCUMENTS

| 3,534,041 A | 10/1970 | van der Berg et al. |
| 5,972,837 A | 10/1999 | Shōko et al. |

FOREIGN PATENT DOCUMENTS

| EP | 474589 | 3/1992 |
| WO | WO 96/40097 | 12/1996 |
| WO | 97/28005 | 8/1997 |
| WO | WO 97/46511 | 12/1997 |
| WO | WO 99/29657 | 6/1999 |

OTHER PUBLICATIONS

Pop et al., *Versatile Acylation of N–Nucleophiles Using a New Polymer–Supported 1–Hydroxybenzotriazole Derivative*, J. Org. Chem., vol. 62, pp. 2594–2603 (1997).

DeVries et al., *Potential Antiatherosclerotic Agents 6, Hypocholesterolemic Trisubstituted Urea Analogues*, J. Med. Chem., vol. 32, pp. 2318–2325 (1989).

Endo et al., *Anionic [3,3], [2,3] and [1,2] Rearrangement-spof Aliphatic and Aromatic Acyl Hydrazines with N–N Bond Cleavage*, Tetrahedron Letters, vol. 38, No. 12, pp. 2113–2116. (1997).

Christensen et al., *Transient gene expression in mammalian cells grown in serum–free suspension culture*, Cytotechnology, vol. 15, pp. 1–13 (1998).

Derwent Abstract of EP 474,589 (Document B1).

*Primary Examiner*—Theordore J. Criares
(74) *Attorney, Agent, or Firm*—George W. Johnston; Patricia S. Rocha-Tramaloni

(57) ABSTRACT

The present invention is concerned with the use of carbonylamino derivatives of the formula

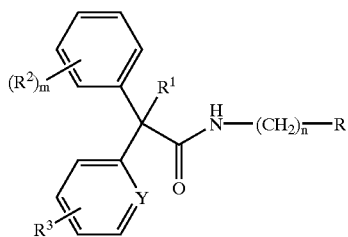

I wherein

R signifies lower alkyl, lower alkenyl, lower alkinyl, cycloalkyl, lower alkoxy or $CF_3$;

$R^1$ signifies hydrogen or lower alkyl;

$R^2$ and $R^3$ signify, independently from each other, hydrogen, halogen or nitro;

Y signifies CH or N;

n is 0–6;

m is 0–2;

as well as with their pharmaceutically acceptable salts for the treatment of diseases, which relate to metabotropic glutamate receptor antagonists and/or agonists.

5 Claims, No Drawings

METHOD FOR TREATING CONDITIONS RELATED TO THE GLUTAMATE RECEPTOR USING CARBOXYLIC ACID AMIDE DERIVATIVES

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs' are known and of these some even have sub-types. On the basis of structural parameters, the different second messager signalling pathways and the different affinity to low-molecular weight chemical compounds, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression.

SUMMARY OF THE INVENTION

The present invention is concerned with the use of carbonylamino derivatives of the formula

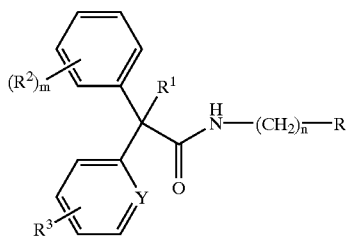

I wherein
R signifies lower alkyl, lower alkenyl, lower alkinyl, cycloalkyl, lower alkoxy or $CF_3$;
$R^1$ signifies hydrogen or lower alkyl;
$R^2$ and $R^3$ signify, independently from each other, hydrogen, halogen or nitro;
Y signifies CH or N;
n is 0–6;
m is 0–2;
as well as with their pharmaceutically acceptable salts.

Encompassed by the present formula I are the following chemical structures:

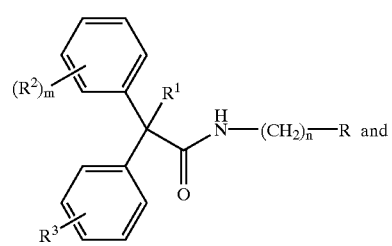

I-1

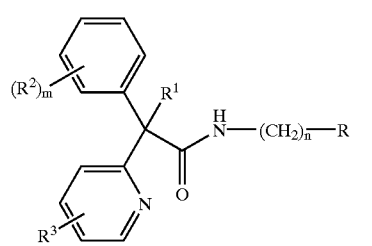

I-2 wherein the substituents $R^1$–$R^3$, R and n and m are given above.

These compounds and their salts are known compounds and they are described per se or with similar structures in the following documents:

WO 9728005; J. Org. Chem., 62(8), 2594, (1997); Tetrahedron Letters, 38(12), 2113, 1997; EP 0 474 589; J. Med. Chem., 32(10), 2318, (1989) and U.S. Pat. No. 3,534,041.

The use as mentioned below is not described in these documents.

It has now surprisingly been found that the compounds of formula I are metabotropic glutamate receptor antagonists or agonists.

DETAILED DESCRIPTION OF THE INVENTION

Objects of the present invention are the use of compounds of formula I and their pharmaceutically acceptable salts in the treatment or prophylaxis of diseases, caused by activation of metabotropic glutamate receptors ligands, medicaments, containing a compound of formula I or a pharmaceutically acceptable acid addition salt thereof, and the use of compounds of formula I for the manufacture of corresponding medicaments.

Preferred compounds of formula I-1 in the scope of the present invention are those, in which Y is CH.

The following are examples of such compounds:
N-pentyl-2,2-diphenyl-acetamide,
N-hexyl-2,2-diphenyl-acetamide,
N-cyclopropylmethyl-2,2-diphenyl-acetamide and
N-hex-2-enyl-2,2-diphenyl-acetamide.

Further preferred are compounds of formula I-2, wherein Y is N, for example the following compounds:

(RS)-N-cyclopropylmethyl-2-phenyl-2-pyridin-2-yl-acetamide, (RS)-2-(3,4-difluoro-phenyl)-N-hexyl-2-pyridin-2-yl-acetamide and (RS)-N-hexyl-2-(4-nitrophenyl)-2-pyridin-3-yl-acetamide.

The invention embraces all stereoisomeric forms in addition to the racemates.

Accordingly, this invention is directed to a method of treating or preventing a condition related to group I metabotropic glutamate receptor activation which comprises administering a compound of the formula

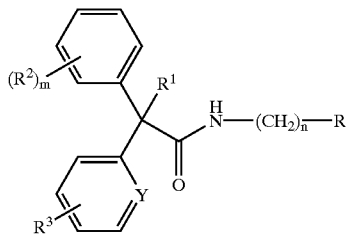

wherein

R signifies lower alkyl, lower alkenyl, lower alkinyl, cycloalkyl, lower alkoxy or $CF_3$;

$R^1$ signifies hydrogen or lower alkyl;

$R^2$ and $R^3$ signify, independently from each other, hydrogen, halogen or nitro;

Y signifies CH or N;

n is 0–6 and m is 0–2 as well as pharmaceutically acceptable salts in an amount effective to alleviate or to prevent said condition Preferably the method of treating or preventing involves administering a compound of formula

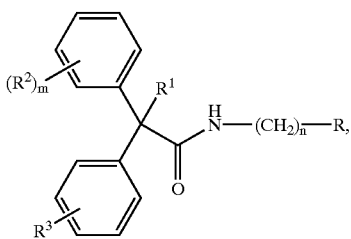

especially a compound selected from the group of

N-pentyl-2,2-diphenyl-acetamide,

N-hexyl-2,2-diphenyl-acetamide,

N-cyclopropylmethyl-2,2-diphenyl-acetamide and

N-hex-2-enyl-2,2-diphenyl-acetamide, or a compound of formula

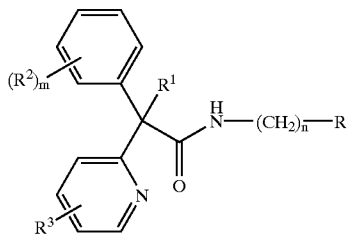

especially a compound selected from the group of (RS)-N-cyclopropylmethyl-2-phenyl-2-pyridin-2-yl-acetamide, (RS)-2-(3,4-difluoro-phenyl)-N-hexyl-2-pyridin-2-yl-acetamide and (RS)-N-hexyl-2-(4-nitrophenyl)-2-pyridin-3-yl-acetamide.

Preferred conditions for treatment or prevention are psychosis, schizophrenia, Alzheimer's disease, cognitive disorders, memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, Huntington's chorea, amyotrophic lateral sclerosis (ALS), dementia caused by AIDS, eye injuries, retinopathy, idiopathic Parkinsonism or Parkinsonism caused by medicaments, muscle spasms, convulsions, migraine, urinary incontinence, nicotine addiction, opiate addiction, anxiety, vomiting, dyskinesia and depression.

This invention also includes pharmaceutical compositions which contain one or more compounds of the formula

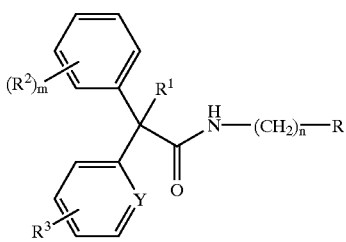

wherein

R signifies lower alkyl, lower alkenyl, lower alkinyl, cycloalkyl, lower alkoxy or $CF_3$;

$R^1$ signifies hydrogen or lower alkyl;

$R^2$ and $R^3$ signify, independently from each other, hydrogen, halogen or nitro;

Y signifies CH or N;

n is 0–6 and m is 0–2 as well as pharmaceutically acceptable salts; and a pharmaceutically acceptable carrier.

Preferred compositions comprise a compound of formula

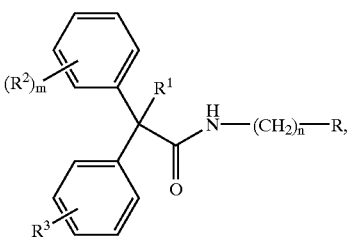

I-1 especially one or more of
N-pentyl-2,2-diphenyl-acetamide,
N-hexyl-2,2-diphenyl-acetamide,
N-cyclopropylmethyl-2,2-diphenyl-acetamide and
N-hex-2-enyl-2,2-diphenyl-acetamide,
or a compound of the formula

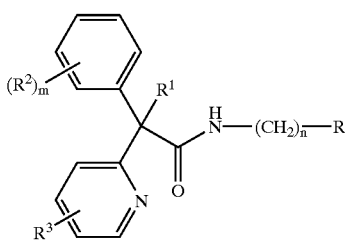

I-2 especially one or more of
(RS)-N-cyclopropylmethyl-2-phenyl-2-pyridin-2-yl-acetamide,
(RS)-2-(3,4-difluoro-phenyl)-N-hexyl-2-pyridin-2-yl-acetamide and
(RS)-N-hexyl-2-(4-nitrophenyl)-2-pyridin-3-yl-acetamide.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "lower alkenyl" denotes an alkylene group having from 2 to 7 carbon atoms with a double bond between any two adjacent carbon atoms, preferably with 1 ot 4 carbon atoms.

The term "lower alkinyl" denotes an alkylene group having from 2 to 7 carbon atoms with a triple bond located between any two adjacent carbon atoms, preferably with 1 to 4 carbon atoms.

The term "cycloalkyl" denotes a saturated hydrocarbon ring having from 3 to 8 carbon atoms, preferably from 3 to 5 carbon atoms.

The term "lower alkoxy" denotes a lower alkyl residue in the sense of the foregoing definition bonded via an oxygen atom.

The term "halogen" embraces fluorine, chlorine, bromine and iodine.

The phrase "condition related to group I metabotropic glutamate receptor activation" denotes conditions such as those listed above which produce undesirable physiological symptoms related to group I metabotropic glutamate receptor activity, whether excessive or insufficient.

The phrase "an amount effective to alleviate" or "an amount effective to prevent" means the amount of compound which when administered to an individual patient reduces undesirable physiological symptoms related to group I metabotropic glutamate receptor activity, or prevents such symptoms from arising. Reduction in pain, spasm, or vomiting would be examples of alleviation. Examples of prevention would be no restriction in brain function resulting from lack of oxygen to the brain after trauma, or transplant or bypass, or lack of Parkinsonian symptoms after administration of a medicament which causes such symptoms.

The compounds of formula I and their pharmaceutically acceptable salts can be manufactured by processes, known in the art, for example by the following scheme:

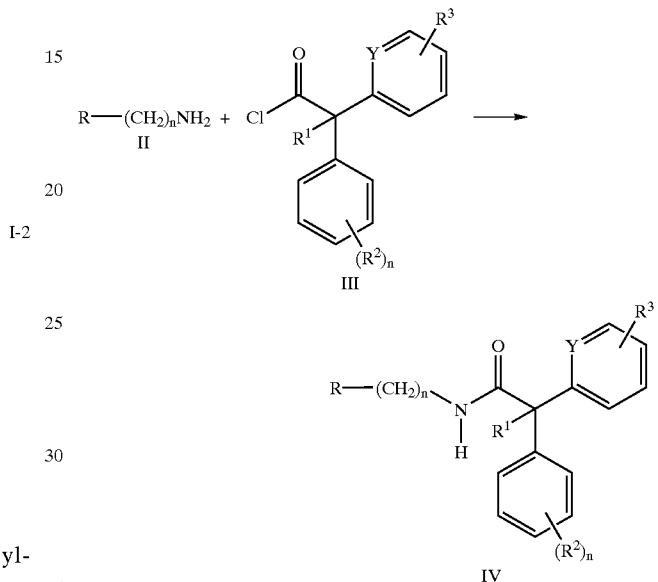

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation or pharmaceutically acceptable salts of acidic compounds.

The scheme gives an overview of the manufacture of the compounds of formula I starting from-known compounds. The manufacture of representative compounds of formula I is described in detail in examples 1–28.

The compounds of formula I and their pharmaceutically acceptable salts are, as already mentioned above, metabotropic glutamate receptor agonists or antagonists and can be used for the treatment or prevention of acute or chronic neurological disorders, such as psychosis, schizophrenia, Alzheimer's disease, cognitive diorders and memory deficits, as well as acute and chronic pain. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Alzheimer's disease, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGlu receptor agonists and/or antagonists. It has been found that compounds of examples 1, 2, 5, 7–10, 12–21, 23, 24 and 28 are agonists. The remaining compounds have been identified as being antagonists. The compounds show activities, as measured in the assay described below.

The compounds of the present invention are group I mGlu receptor agonists and/or antagonists. The compounds show activities, as measured in the assay described below, of 50 $\mu$M or less, typically 1 $\mu$M or less, and ideally of 0.5 $\mu$M or less.

Compounds of examples 3, 4, 6, 11, 22, 25, 26 and 27 show an antagonistic activity, the remaining compounds are agonists on the group 1 mGluR.

The following $EC_{50}$ values have been measured:

| Example | $EC_{50}$ ($\mu$M) |
|---------|---------------------|
| 2 | 2.12 |
| 3 | 12.7 |
| 4 | 1.0 |
| 7 | 17.0 |
| 19 | 2.98 |
| 21 | 3.13 |
| 26 | 15.0 |

Test Method cDNA encoding for rat mGlu1a receptor obtained from Prof. S. Nakanishi (Kyoto, Japan) was transiently transfected into EBNA cells using a procedure described by E. -J. Schlaeger and K. Christensen ("Transient gene expression in mammalian cells grown in serum-free suspension culture," Cytotechnology, 15: 1–13, 1998).

$[Ca^{2+}]i$ measurement were performed on mGlu1a transfected EBNA cells after incubation of the cells with Fluo-3 AM (0.5 $\mu$M final concentration) for 1 hour at 37° C. followed by 4 washes with assay buffer (DMEM supplemented with Hank's salt and 20 mM HEPES). $[Ca^{2+}]i$ measurement were done using a fluorometric imaging plate reader (FLIPR, Molecular Devices Corporation, La Jolla, Calif., USA). When compounds were evaluated as antagonists they were tested against 10 $\mu$M glutamate as agonist.

The inhibition (antagonists) or activation (agonists) curves were fitted with a four parameter logistic equation giving $EC_{50}$, $IC_{50}$ and Hill coefficient using the iterative non linear curve fitting software Origin (Microcal Software Inc., Northampton, Mass., USA).

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/ kg/day being preferred for all of the indications described. The daily dosage for an adult human being weighing 70 kg accordingly lies between 0.7–1400 mg per day, preferably between 7 and 700 mg per day.

The examples which follow serve to illustrate the invention and are not intended to limit it in anyway.

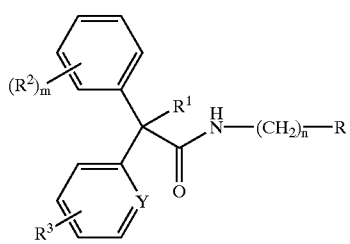

I

| Y | R | $R^1$ | $R^2$ | $R^3$ | n | m | Example No. |
|---|---|-------|-------|-------|---|---|-------------|
| CH | $CH_3$ | H | H | H | 4 | 0 | 1 |
| CH | $CH_3$ | H | H | H | 2 | 0 | 2 |
| CH | $CH_3$ | $CH_3$ | H | H | 2 | 0 | 3 |
| CH | $CH_3$ | $CH_3$ | H | H | 4 | 0 | 4 |
| CH | $CH_3$ | H | H | H | 3 | 0 | 5 |
| CH | $CH_3$ | $CH_3$ | H | H | 3 | 0 | 6 |

-continued

| Y | R | R¹ | R² | R³ | n | m | Example No. |
|---|---|----|----|----|---|---|-------------|
| CH | cyclopropyl | H | H | H | 0 | 0 | 7 |
| CH | CH₃ | H | H | H | 6 | 0 | 8 |
| CH | CH₃ | H | H | H | 5 | 0 | 9 |
| CH | cyclopropyl | H | H | H | 1 | 0 | 10 |
| CH | cyclopropyl | CH₃ | H | H | 1 | 0 | 11 |
| CH | CH₃ | H | H | H | 1 | 0 | 12 |
| CH | —CH=CH₂ | H | H | H | 1 | 0 | 13 |
| CH | —≡H | H | H | H | 1 | 0 | 14 |
| CH | —CH(CH₃)₂ | H | H | H | 2 | 0 | 15 |
| CH | —CH=CH—(CH₂)₂—CH₃ | H | H | H | 1 | 0 | 16 |
| CH | —CH=CH—CH₃ | H | H | H | 3 | 0 | 17 |
| CH | —OCH₃ | H | H | H | 5 | 0 | 18 |
| CH | —OCH₃ | H | H | H | 4 | 0 | 19 |
| CH | —OCH₂CH₃ | H | H | H | 2 | 0 | 20 |
| CH | —O(CH₂)₂CH₃ | H | H | H | 2 | 0 | 21 |
| N | cyclopropyl | H | H | H | 1 | 0 | 22 |
| N | CH₃ | H | F | H | 5 | 2 | 23 |
| N | CH₃ | H | NO₂ | H | 5 | 1 | 24 |
| CH | cyclobutyl | CH₃ | H | H | 1 | 0 | 25 |
| CH | —CF₃ | H | H | H | 3 | 0 | 26 |
| CH | CF₃ | CH₃ | H | H | 3 | 0 | 27 |
| CH | —≡H | H | H | H | 3 | 0 | 28 |

EXAMPLE 1
N-Pentyl-2,2-diphenyl-acetamide

To a cooled (0° C.) solution diphenylacetyl chloride (1.73 mmol) and pyridine (0.28 ml, 3.46 mmol) in dichloromethane (12 ml) was added pentylamine (0.39 ml, 2.60 mmol) and the reaction mixture was stirred at RT for 16 h. Aqueous work up and crystallization from ethyl acetate/hexane yielded the product as a light yellow solid, m.p. 101° C. and MS: m/e=281 (M⁺).

EXAMPLE 2
2,2-Diphenyl-N-propyl-acetamide

The title compound, light yellow solid, m.p. 90° C. and MS: m/e=254 (M⁺) was prepared in accordance with the general method of example 1 from diphenylacetyl chloride and propylamine.

EXAMPLE 3
2,2-Diphenyl-N-propyl-propionamide

The title compound, white solid, m.p. 62° C. and MS: m/e=267 (M⁺) was prepared in accordance with the general method of example 1 from 2,2-diphenylpropionyl chloride and propylamine.

EXAMPLE 4
N-Pentyl-2,2-diphenyl-propionamide

The title compound, colorless oil, MS: m/e=295 (M⁺) was prepared in accordance with the general method of example 1 from 2,2-diphenylpropionyl chloride and pentylamine.

EXAMPLE 5
N-Butyl-2,2-diphenyl-acetamide

The title compound, white solid, m.p. 96° C. and MS: m/e=268.4 (M+H⁺) was prepared in accordance with the general method of example 1 from diphenylacetyl chloride and butylamine.

EXAMPLE 6
N-Butyl-2,2-diphenyl-propionamide

The title compound, colorless oil, MS: m/e=282.2 (M+H⁺) was prepared in accordance with the general method of example 1 from 2,2-diphenylpropionyl chloride and butylamine.

EXAMPLE 7
N-Cyclopropyl-2,2-diphenyl-acetamide

The title compound, white solid, m.p. 292° C. and MS: m/e=251 (M⁺) was prepared in accordance with the general method of example 1 from diphenylacetyl chloride and cyclopropylamine.

EXAMPLE 8
N-Heptyl-2,2-diphenyl-acetamide

The title compound, white solid, m.p. 90° C. and MS: m/e=309 (M⁺) was prepared in accordance with the general method of example 1 from diphenylacetyl chloride and heptylamine.

EXAMPLE 9
N-Hexyl-2,2-diphenyl-acetamide

The title compound, off-white solid, m.p. 100° C. and MS: m/e=296.4 (M+H⁺) was prepared in accordance with the general method of example 1 from diphenylacetyl chloride and hexylamine.

EXAMPLE 10
N-Cyclopropylmethyl-2,2-diphenyl-acetamide

The title compound, white solid, m.p. 130° C. and MS: m/e=265 (M⁺) was prepared in accordance with the general method of example 1 from diphenylacetyl chloride and cyclopropylmethylamine.

EXAMPLE 11
N-Cyclopropylmethyl-2,2-diphenyl-propionamide

The title compound, white solid, m.p. 380° C. and MS: m/e=279 (M⁺) was prepared in accordance with the general method of example 1 from 2,2-diphenylpropionyl chloride and cyclopropylmethylamine.

EXAMPLE 12
N-Ethyl-2,2-diphenyl-acetamide

The title compound, off-white solid, m.p. 87° C. and MS: m/e=239 (M⁺) was prepared in accordance with the general method of example 1 from diphenylacetyl chloride and ethylamine.

EXAMPLE 13
N-Allyl-2,2-diphenyl-acetamide

The title compound, white solid, m.p. 186° C. and MS: m/e=251 (M+) was prepared in accordance with the general method of example 1 from diphenylacetyl chloride and allylamine.

EXAMPLE 14
2,2-Diphenyl-N-prop-2-ynyl-acetamide

The title compound, white solid, m.p. 131° C. and MS: m/e=249 (M+) was prepared in accordance with the general method of example 1 from diphenylacetyl chloride and prop-2-ynylamine.

EXAMPLE 15
N-(3-Methyl-butyl)-2,2-diphenyl-acetamide

The title compound, white solid, m.p. 128° C. and MS: m/e=281 (M+) was prepared in accordance with the general method of example 1 from diphenylacetyl chloride and 3-methyl-butylamine.

EXAMPLE 16
N-Hex-2-enyl-2,2-diphenyl-acetamide

The title compound, white solid, m.p. 81° C. and MS: m/e=293 (M+) was prepared in accordance with the general method of example 1 from diphenylacetyl chloride and hex-2-enylamine.

EXAMPLE 17
N-Hex-4-enyl-2,2-diphenyl-acetamide

The title compound, white solid, m.p. 85° C. and MS: m/e=293 (M+) was prepared in accordance with the general method of example 1 from diphenylacetyl chloride and hex-4-enylamine.

EXAMPLE 18
N-(5-Methoxy-pentyl)-2,2-diphenyl-acetamide

The title compound, white solid, m.p. 74.2–75.0° C. and MS: m/e=312 (M+H+) was prepared in accordance with the general method of example 1 from diphenylacetyl chloride and 5-methoxy-pentylamine.

EXAMPLE 19
N-(4-Methoxy-butyl)-2,2-diphenyl-acetamide

The title compound, white solid, m.p. 75.5–76.8° C. and MS: m/e=298 (M+H+) was prepared in accordance with the general method of example 1 from diphenylacetyl chloride and 4-methoxy-butylamine.

EXAMPLE 20
N-(2-Ethoxy-ethyl)-2,2-diphenyl-acetamide

The title compound, white solid, m.p. 83.5–86.2° C. and MS: m/e=283 (M+H+) was prepared in accordance with the general method of example 1 from diphenylacetyl chloride and 2-ethoxy-ethylamine.

EXAMPLE 21
2,2-Diphenyl-N-(2-propoxy-ethyl)-acetamide

The title compound, white solid, m.p. 77.8–78.9° C. and MS: m/e=297 (M+) was prepared in accordance with the general method of example 1 from diphenylacetyl chloride and 2-propoxy-ethylamine.

EXAMPLE 22
(RS)-N-Cyclopropylmethyl-2-phenyl-2-pyridin-2-yl-acetamide a) To a solution of (RS)-phenyl-pyridin-2-yl-acetic acid methyl ester (0.051 g, 0.22 mmol) in 3 ml of aminomethyl cyclopropane was added 4 mg (0.02 mmol) of anhydrous p-toluenesulfonic acid and the reaction mixture was heated to 83° C. (reflux) for 16 h. Aqueous work up with ethyl acetate/water and evaporation of the solvents in vaccuo yielded the product (0.040 g, 66%) as an orange oil, MS: m/e=295 (M+).

The starting material (RS)-phenyl-pyridin-2-yl-acetic acid methyl ester was obtained as follows:

b) To a solution of benzyl cyanide (5.00 g, 42.7 mmol) and 2-chloropyridine (4.85 g, 42.7 mmol) in 15 ml of toluene was added finely powdered sodium amide (3.33 g, 85.4 mmol) in portions keeping the temperature between 20–30° C. The suspension was refluxed for 6 h. After cooling, 100 ml water is added and the product is worked up with ethyl acetate/water. After drying (MgSO4) and concentration, the crude material is purified by flash chromatography on silicagel using a 1:4 mixture of ethyl acetate and hexane as eluant to yield 3.40 g (17.5 mmol, 41%) of (RS)-phenyl-pyridin-2-yl-acetonitrile as a white solid, m.p. 89° C. and MS: m/e=194 (M+).

c) A solution of (RS)-phenyl-pyridin-2-yl-acetonitrile (0.928 g, 4.80 mmol) in 5 ml of conc. sulfuric acid was stirred overnight at room temperature. The mixture is poured on 100 g of ice, the pH is adjusted to 8–9 by addition of 28% sodium hydroxide solution and the product is extracted with ethyl acetate/water. After drying (MgSO4) and concentration, the crude material is purified by flash chromatography on silicagel using ethyl acetate as eluant to yield 0.878 g (4.14 mmol, 86%) of (RS)-phenyl-pyridin-2-yl-acetamide as a white solid, m.p. 134° C. and MS: m/e=213.2 (M+H+).

d) (RS)-Phenyl-pyridin-2-yl-acetamide (0.340 g, 1.60 mmol) was dissolved in 5 ml of a saturated solution of HCl/methanol and refluxed for 6 h in a closed vessel. The mixture is poured on 25 g of ice, the pH is adjusted to 8–9 by cautious addition of 28% sodium hydroxide solution keeping the temperature below 10° C. and the product is extracted with ethyl acetate/water. After drying (MgSO4) and concentration, the crude material is purified by flash chromatography on silicagel using 1:4 mixture of ethyl acetate and hexane as eluant to yield 0.204 g (0.939 mmol, 59%) of (RS)-phenyl-pyridin-2-yl-acetic acid methyl ester as a white solid, m.p. 74° C. and MS: m/e=228.2 (M+H+).

EXAMPLE 23
(RS)-2-(3,4-Difluoro-phenyl)-N-hexyl-2-pyridin-2-yl-acetamide

The title compound, amorphous, MS: m/e=333.3 (M+H+) was prepared in accordance with the general method of example 22(a) from (RS)-2-(3,4-difluoro-phenyl)-2-pyridin-2-yl-acetic acid methyl ester and hexylamine.

The starting material (RS)-2-(3,4-difluoro-phenyl)-2-pyridin-2-yl-acetic acid methyl ester was prepared in accordance with the general methods described in example 22(b-d) whereby (3,4-difluorophenyl)-acetonitrile instead of phenylacetonitrile was used.

One obtains impure (RS)-(3,4-difluoro-phenyl)-pyridin-2-yl-acetonitrile as a red viscous oil, MS: m/e=230 (M+), which was directly used in the next step.

(RS)-(3,4-Difluoro-phenyl)-pyridin-2-yl-acetamide was obtained as a white solid, m.p. 123–124° C., MS: m/e=248 (M+).

One obtains (RS)-(3,4-difluoro-phenyl)-pyridin-2-yl-acetic acid methyl ester as a white solid, MS: m/e=248 (M+).

EXAMPLE 24
(RS)-N-Hexyl-2-(4-nitrophenyl)-2-pyridin-3-yl-acetamide

The title compound, yellow viscous oil, MS: m/e=341 (M+) was prepared in accordance with the general method of example 22(a) from (RS)-2-(4-nitrophenyl)-2-pyridin-2-yl-acetic acid methyl ester and hexylamine.

The starting material (RS)-2-(4-nitrophenyl)-2-pyridin-2-yl-acetic acid methyl ester was prepared in accordance with the general methods described in example 22(b-d) whereby (4-nitro-phenyl)-acetonitrile instead of phenylacetonitrile was used.

(RS)-(4-nitrophenyl)-pyridin-2-yl-acetonitrile was obtained as a dark red solid, m.p. 97–99° C., MS: m/e=239 ($M^+$).

One obtains (RS)-(4-nitrophenyl)-pyridin-2-yl-acetamide as a beige solid, m.p. 155–156° C., MS: m/e=257 ($M^+$).

One obtains (RS)-(4-nitrophenyl)-pyridin-2-yl-acetic acid methyl ester as a red viscous oil, MS: m/e=273.2 ($M+H^+$).

EXAMPLE 25

N-Cyclobutylmethyl-2,2-diphenyl-propionamide

The title compound, white solid, m.p. 79° C. and MS: m/e=294.4 ($M+H^+$) was prepared in accordance with the general method of example 1 from 2,2-diphenylpropionyl chloride and cyclobutyl methylamine.

EXAMPLE 26

2,2-Diphenyl-N-(4,4,4-trifluoro-butyl)-acetamide

The title compound, white solid, m.p. 166° C. and MS: m/e=321 ($M^+$) was prepared in accordance with the general method of example 1 from diphenylacetyl chloride and 4,4,4-trifluoro-butylamine.

EXAMPLE 27

2,2-Diphenyl-N-(4,4,4-trifluoro-butyl)-propionamide

The title compound, white solid, m.p. 82° C. and MS: m/e=336.2 ($M+H^+$) was prepared in accordance with the general method of example 1 from 2,2-diphenylpropionyl chloride and 4,4,4-trifluorobutyl-amine.

EXAMPLE 28

N-Pent-4-ynyl-2,2-diphenyl-acetamide

The title compound, white solid, m.p. 90° C. and MS: m/e=278.2 ($M+H^+$) was prepared in accordance with the general method of example 1 from diphenylacetyl chloride and pent-4-ynyl-amine.

Example A

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example B

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example C

Capsules of the following composition are produced:

|  | mg/Capsule |
| --- | --- |
| Active ingredient | 50 |
| Crystalline. lactose | 60 |
| Mirocrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A pharmaceutical composition which comprises a compound of the formula

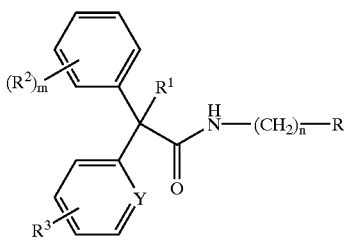

I wherein

R signifies lower alkyl, lower alkenyl, lower alkinyl, cycloalkyl, lower alkoxy or $CF_3$;

$R^1$ signifies hydrogen or lower alkyl;

$R^2$ and $R^3$ signify, independently from each other, hydrogen, halogen or nitro;

Y signifies CH or N, with the proviso that when Y is CH, neither $R^2$ nor $R^3$ are halogen;

n is 0–6;

m is 0–2;

or a pharmaceutically acceptable salt thereof; and a pharmaceutically acceptable carrier.

2. A pharmaceutical composition of claim 1 which comprises a compound of formula

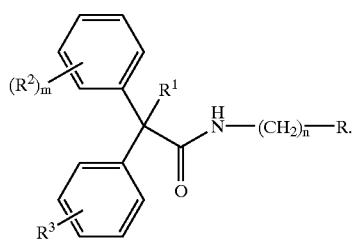

I-1

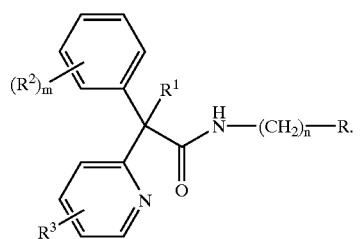

I-2

3. A pharmaceutical composition of claim 2 which comprises one or more of

N-pentyl-2,2-diphenyl-acetamide,
N-hexyl-2,2-diphenyl-acetamide,
N-cyclopropylmethyl-2,2-diphenyl-acetamide and
N-hex-2-enyl-2,2-diphenyl-acetamide.

4. A pharmaceutical composition of claim 1 which comprises a compound of the formula 5. A pharmaceutical composition of claim 4 which comprises one or more of (RS)-N-cyclopropylmethyl-2-phenyl-2-pyridin-2-yl-acetamide,
(RS)-2-(3,4-difluoro-phenyl)-N-hexyl-2-pyridin-2-yl-acetamide and
(RS)-N-hexyl-2-(4-nitrophenyl)-2-pyridin-3-yl-acetamide.

* * * * *